(12) United States Patent
Zhao

(10) Patent No.: US 8,800,568 B1
(45) Date of Patent: Aug. 12, 2014

(54) TEETH SEPARATING SYSTEM

(76) Inventor: Sherry Zhao, Tampa, FL (US)

( * ) Notice: Subject to any disclaimer, the term of this patent is extended or adjusted under 35 U.S.C. 154(b) by 0 days.

(21) Appl. No.: 13/200,469

(22) Filed: Sep. 23, 2011

Related U.S. Application Data

(63) Continuation-in-part of application No. 12/930,905, filed on Jan. 19, 2011, now abandoned.

(51) Int. Cl.
*A61C 5/14* (2006.01)
*A61C 3/00* (2006.01)

(52) U.S. Cl.
USPC .............................. 128/861; 433/6

(58) Field of Classification Search
USPC ................... 128/861, 859, 857, 846; 433/6, 2
See application file for complete search history.

(56) References Cited

U.S. PATENT DOCUMENTS

| | | | | |
|---|---|---|---|---|
| 5,277,203 | A * | 1/1994 | Hays .............................. | 128/861 |
| 7,210,483 | B1 * | 5/2007 | Lesniak et ..................... | 128/861 |
| 8,007,277 | B2 * | 8/2011 | Fischer et al. ................ | 128/861 |
| 2004/0103905 | A1 * | 6/2004 | Farrell .......................... | 128/861 |

* cited by examiner

*Primary Examiner* — Patricia Bianco
*Assistant Examiner* — Tarla Patel

(57) ABSTRACT

An arcuate base section with upper and lower surfaces separated by a thickness has an arcuate exterior periphery with a central front point and laterally spaced rear points, an arcuate interior periphery generally concentric with the exterior periphery, a width and a depth. Two lateral support sections and a central support section are in an arcuate configuration and have inner and outer surfaces separated by a thickness. The support sections have free upper edges and lower edge separated by a height. The lateral support sections are perpendicular to and integrally formed with the base section at the exterior periphery adjacent to the rear points. The central support section is perpendicular to and integrally formed with the base section at the interior periphery adjacent to the central front point. The system is fabricated in one piece of a material with limited flexibility and elasticity.

1 Claim, 4 Drawing Sheets

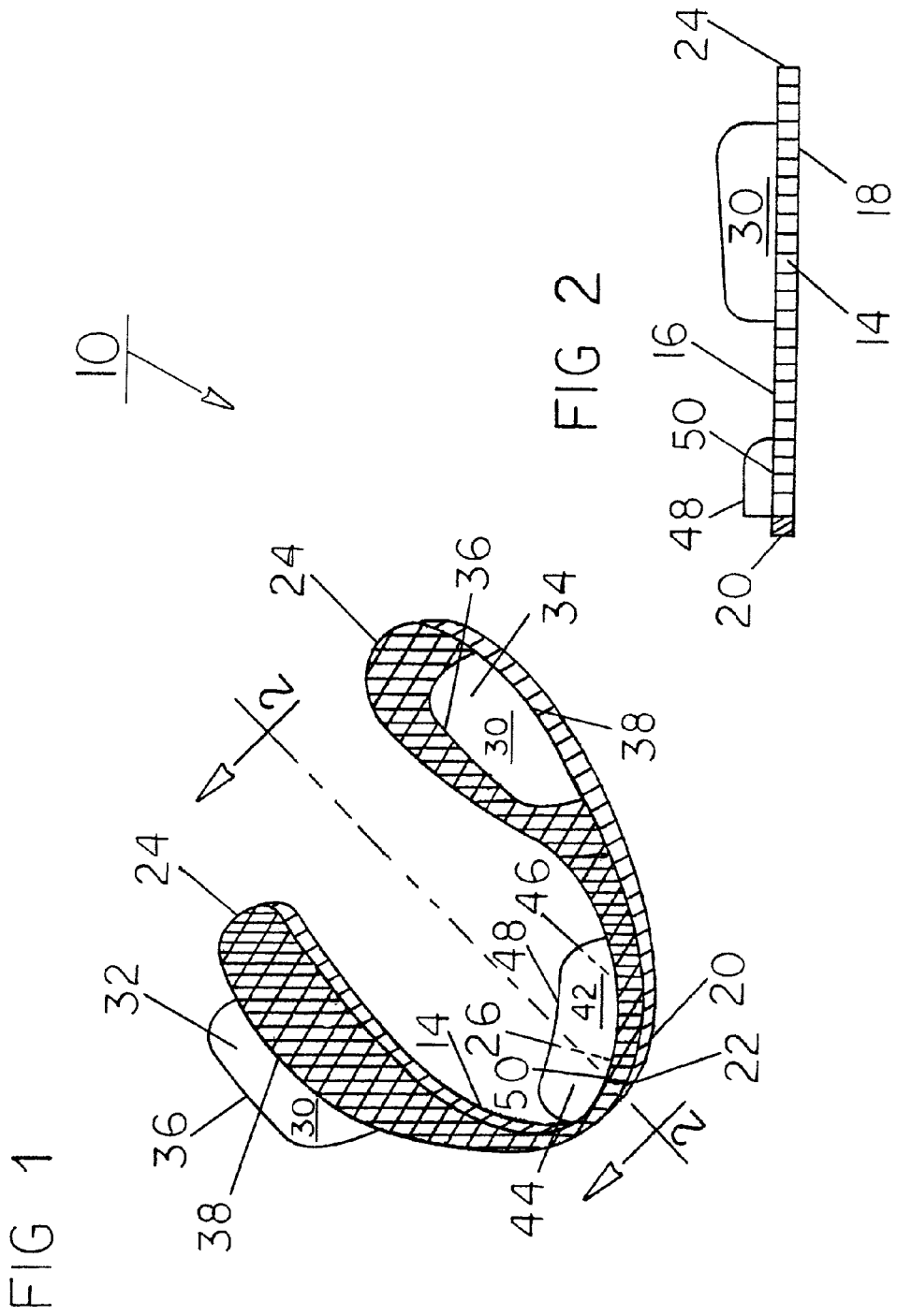

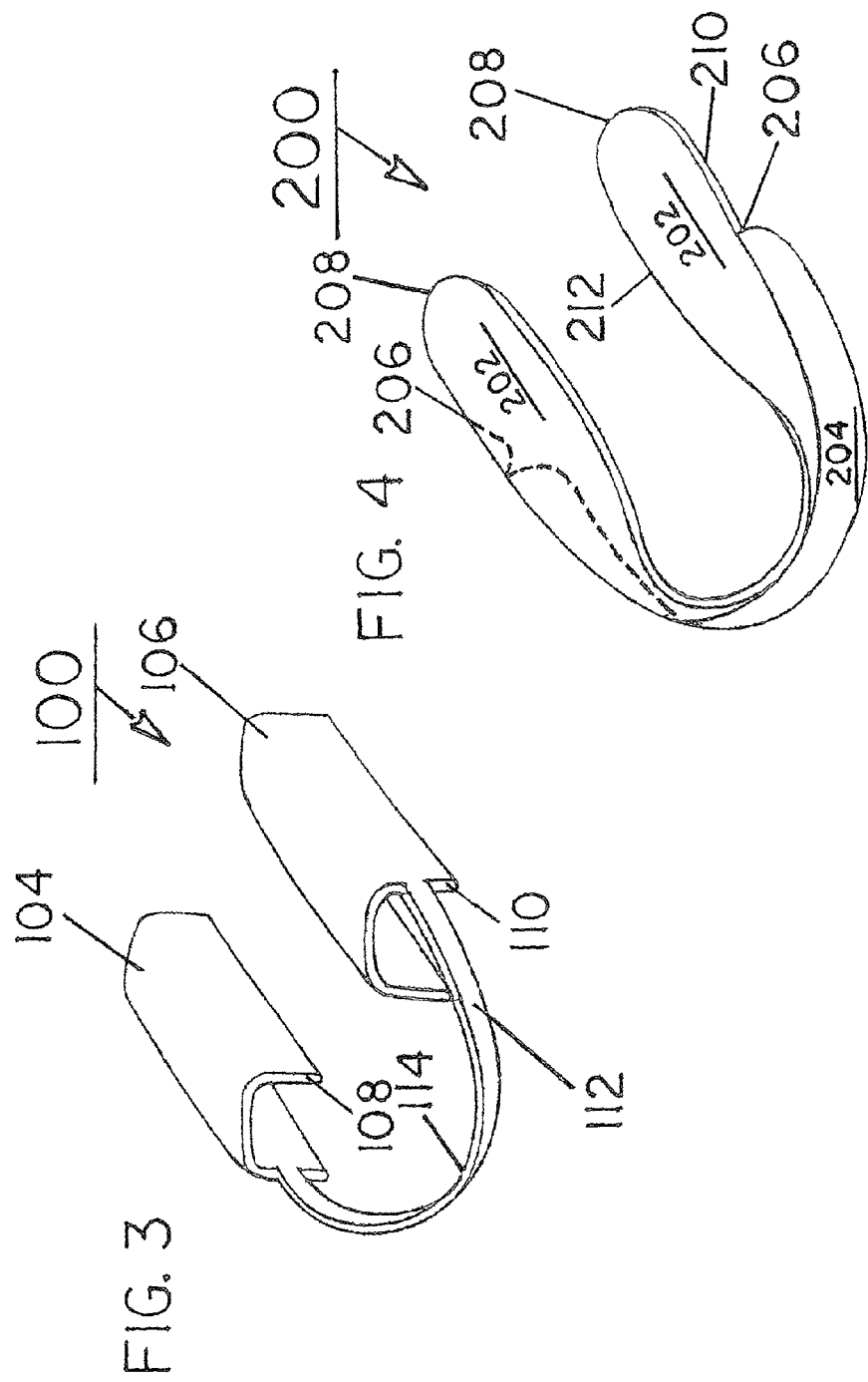

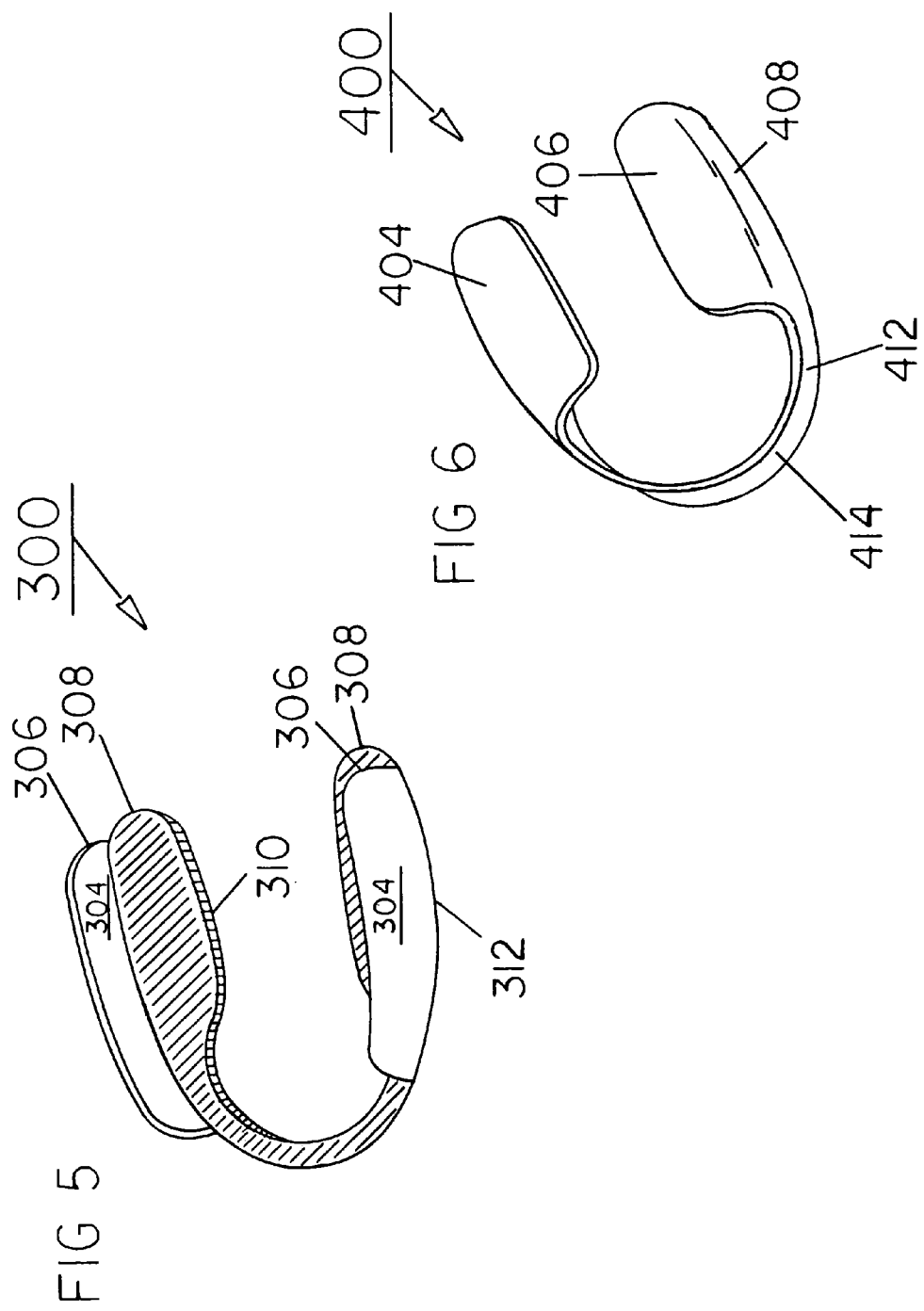

TEETH SEPARATING SYSTEM

RELATED APPLICATION

The present application is a continuation-in-part of patent application Ser. No. 12/930,905 filed Jan. 19, 2011 now abandoned, the subject matter of which is incorporated herein by reference.

BACKGROUND OF THE INVENTION

Field of the Invention

The present invention relates to a teeth separating system and more particularly pertains to abating tooth grinding through positioning the system between upper and lower teeth of a user, the abating being done in a safe, convenient and economical manner.

SUMMARY OF THE INVENTION

In view of the disadvantages inherent in the known types of separating systems of known designs and configurations now present in the prior art, the present invention provides an improved teeth separating system. As such, the general purpose of the present invention, which will be described subsequently in greater detail, is to provide a new and improved teeth separating system and method which has all the advantages of the prior art and none of the disadvantages.

To attain this, the present invention essentially comprises a teeth separating system. First provided is a base section. The base section is in an arcuate configuration. The base section is positionable in a generally horizontal plane when in use between the teeth of a user while standing. The base section has an upper surface. The upper surface is positionable in contact with the upper teeth of a user during use. The base section has a lower surface. The lower surface is positionable in contact with the lower teeth of a user during use. The upper surface and lower surface are separated by a thickness between 1.0 and 2.0 millimeters, throughout its entire extent. The base section has an arcuate exterior periphery. The exterior periphery has a central front point. The exterior periphery has laterally spaced rear points. The base section has an arcuate interior periphery. The interior periphery is generally concentric with the exterior periphery. The base section has a width of between 55 and 65 millimeters measured between the end points. The base section has a depth of between 50 and 55 millimeters measured between the central forward point and midway between the end points.

Two lateral support sections are provided next. The lateral support sections are in an arcuate configuration. The lateral support sections are positionable in a generally vertical orientation when in use exterior of gums and interior of the cheeks of a user while standing. The lateral support sections have inner surfaces. The lateral support sections have outer surfaces. The inner and outer surfaces are separated by a thickness of between 0.5 and 1.0 millimeters throughout their entire extent. The lateral support sections have free upper edges. The lateral support sections have lower edges. The upper and lower edges are separated by a height of between 15 and 20 millimeters. The lower edges are provided perpendicular to and integrally formed with the base section at the exterior periphery adjacent to the rear points of the base section. The lateral support sections each have an arcuate length of between 200 percent and 300 percent of the depth of the base section.

Provided last is a single central support section in an arcuate configuration. The central support section is positionable in a generally vertical orientation when in use interior of gums of a user while standing. The central support section has an inner surface and an outer surface. The inner and outer surfaces are separated by a thickness of between 0.5 and 1.0 millimeters throughout its entire extent. The central support section has a free upper edge and a lower edge separated by a height of between 15 and 20 millimeters. The lower edge is perpendicular to and integrally formed with the base section at the interior periphery adjacent to the front point of the base section. The central support section has an arcuate length of between 200 percent and 300 percent of the depth of the base section.

The system is fabricated in one piece of a material with limited flexibility and elasticity. The material is chosen from the class of materials with limited flexibility and elasticity. The class of materials with limited flexibility and elasticity includes silicone and latex and plastic and organic materials.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims attached.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved teeth separating system which has all of the advantages of the prior art separating systems of known designs and configurations and none of the disadvantages.

It is another object of the present invention to provide a new and improved teeth separating system which may be easily and efficiently manufactured and marketed.

It is further object of the present invention to provide a new and improved teeth separating system which is of durable and reliable constructions.

An even further object of the present invention is to provide a new and improved teeth separating system which is susceptible of a low cost of manufacture with regard to both materials and labor, and which accordingly is then susceptible of low prices of sale to the consuming public, thereby making such teeth separating system economically available to the buying public.

Even still another object of the present invention is to provide a teeth separating system for abating tooth grinding through positioning between upper and lower teeth of a user, the abating being done in a safe, convenient and economical manner.

Lastly, it is an object of the present invention to provide a new and improved teeth separating system. A base section in an arcuate configuration has upper and lower surfaces separated by a thickness. The base section has an arcuate exterior periphery with a central front point and laterally spaced rear points. The base section has an arcuate interior periphery generally concentric with the exterior periphery. The base section has a width and a depth. Two lateral support sections and a central support section are in an arcuate configuration and have inner and outer surfaces. The inner and outer surfaces are separated by a thickness. The support sections have free upper edges and lower edge separated by a height. The lateral support sections are perpendicular to and integrally formed with the base section at the exterior periphery adjacent to the rear points. The central support section is perpendicular to and integrally formed with the base section at the interior periphery adjacent to the central front point. The system is fabricated in one piece of a material with limited flexibility and elasticity.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated the preferred and alternate embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a perspective illustration of a teeth separating system constructed in accordance with the principles of the present invention.

FIG. 2 is a side elevational view of the system illustrated in FIG. 1.

FIGS. 3 through 7 are perspective illustrations of alternate embodiments of the invention.

The same reference numerals refer to the same parts throughout the various Figures.

DESCRIPTION OF THE PREFERRED EMBODIMENT

Figure 7:
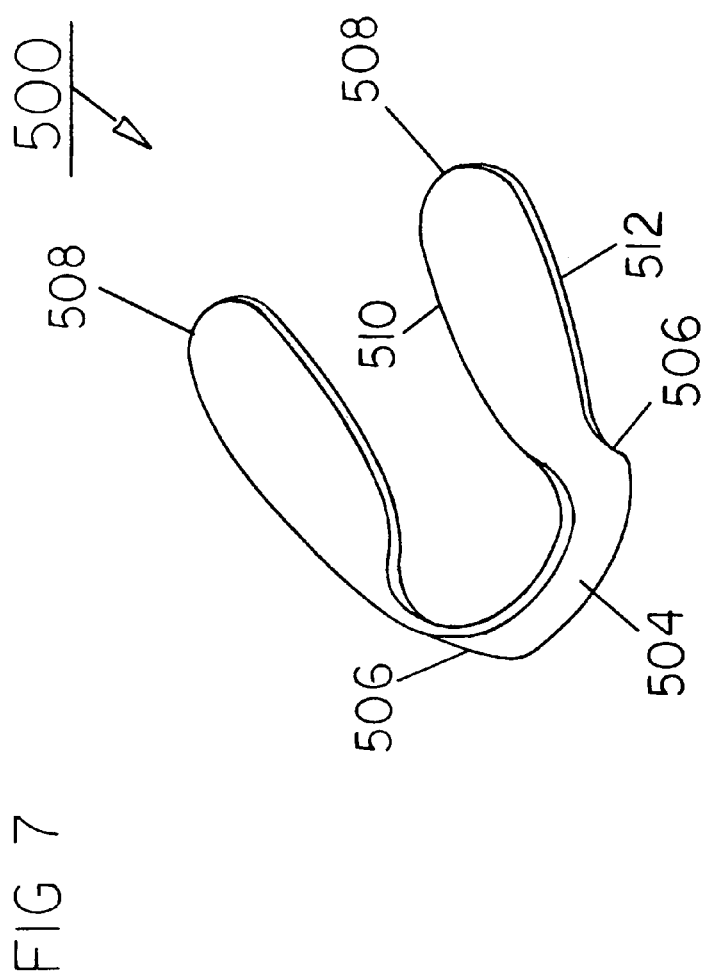

With reference now to the drawings, and in particular to FIG. 1 thereof, the preferred embodiment of the new and improved teeth separating system embodying the principles and concepts of the present invention and generally designated by the reference numeral 10 will be described.

The present invention, the teeth separating system 10 is comprised of a plurality of components. Such components in their broadest context include a base section and a support section. Such components are individually configured and correlated with respect to each other so as to attain the desired objective.

First provided is a base section 14. The base section is in an arcuate configuration. The base section is positionable in a generally horizontal plane when in use between the teeth of a user while standing. The base section has an upper surface 16. The upper surface is positionable in contact with the upper teeth of a user during use. The base section has a lower surface 18. The lower surface is positionable in contact with the lower teeth of a user during use. The upper surface and lower surfaces are separated by a thickness between 1.0 and 2.0 millimeters, throughout its entire extent. The base section has an arcuate exterior periphery 20. The exterior periphery has a central front point 22. The exterior periphery has laterally spaced rear points 24. The base section has an arcuate interior periphery 26. The interior periphery is generally concentric with the exterior periphery. The base section has a width of between 55 and 65 millimeters measured between the end points. The base section has a depth of between 50 and 55 millimeters measured between the central forward point and midway between the end points.

Two lateral support sections 30 are provided next. The lateral support sections are in an arcuate configuration. The lateral support sections are positionable in a generally vertical orientation when in use exterior of gums and interior of the cheeks of a user while standing. The lateral support sections have an inner surface 32. The lateral support sections have an outer surface 34. The inner and outer surfaces are separated by a thickness of between 0.5 and 1.0 millimeters throughout its entire extent. The lateral support sections have a free upper edge 36. The lateral support sections have a lower edge 38. The upper and lower edges are separated by a height of between 15 and 20 millimeters. The lower edge is provided perpendicular to and integrally formed with the base section at the exterior periphery from end to end. The lateral support sections have an arcuate length of between 200 percent and 300 percent of the depth of the base section.

Provided last a single central support section 42 in an arcuate configuration. The central support section is positionable in a generally vertical orientation when in use interior of gums of a user while standing. The central support section having an inner surface 44 and an outer surface 46. The inner and outer surfaces are separated by a thickness of between 0.5 and 1.0 millimeters throughout its entire extent. The central support section has a free upper edge 48 and a lower edge 50 separated by a height of between 15 and 20 millimeter. The lower edge is perpendicular to and integrally formed with the base section at the interior periphery adjacent to the front point of the base section. The central support section has an arcuate length of between 200 percent and 300 percent of the depth of the base section.

The system is fabricated in one piece of a material with limited flexibility and elasticity. The material is chosen from the class of materials with limited flexibility and elasticity. The class of materials with limited flexibility and elasticity includes silicone and latex and plastic and organic materials.

Shown in FIGS. 3 through 7 are perspective illustrations of alternate embodiments of the invention. Each of these alternate embodiments generically features a base section in an arcuate configuration having upper and lower surfaces separated by a thickness. The base section has an arcuate exterior periphery with laterally spaced rear points. The base section also has an arcuate interior periphery generally concentric with the exterior periphery. In addition, the base section has a width and a depth. Also provided is a support section in an arcuate configuration having inner and outer surfaces. The inner and outer surfaces are separated by a thickness. The support section has an upper edge and a lower edge separated by a height. The support section is perpendicular to and integrally formed with the base section at the exterior periphery. The system is fabricated in one piece of a material with limited flexibility and elasticity, the material being chosen from the class of materials with limited flexibility and elasticity including silicone and latex and plastic and organic materials.

FIG. 3 illustrates a system 100 wherein the base section includes two similarly configured spaced sections 104, 106 having a common length. Each spaced section is configured in an inverted U-shaped configuration. Each spaced section has an interior leg 108 positionable interior of a user's gum and an exterior leg 110 positionable exterior of a user's gum. The exterior legs are fabricated integrally with the base section 112. The base section has a forward extent 114 between the support sections. The forward extent has a length greater than the length of the spaced sections.

The system 200 illustrated in FIG. 4 includes a support section 204 in an arcuate configuration with end points 206 spaced forwardly of the rear points 208 of the base section. The interior and exterior peripheries 210, 212 of the base section are laterally spaced a greater distance adjacent to the rear points 208 of the base section than forwardly thereof. The support section 202 depends downwardly from the exterior edge of the base section. The distance between the end points of the support section is greater than the distance between the end points of the support section and the rear points of the base section.

FIG. 5 illustrates an embodiment system 300 wherein the support section 304 is formed of two spaced sections in an arcuate configuration with end points 306 spaced adjacent to the rear points 308 of the base section. The interior and exterior peripheries 310, 312 of the base section are laterally spaced a greater distance adjacent to the rear points 308 of the base section than forwardly thereof. The spaced sections extend upwardly from the exterior edge of the base section adjacent to the rear points of the base sections.

The system 400 is illustrated in FIG. 6. In such system, the base section includes two similarly configured spaced sections 404, 406. The spaced sections have a common length. Each spaced section is configured in an inverted L-shaped configuration. Each spaced section has an exterior leg 408 positionable exterior of a user's gum. The exterior legs are fabricated integrally with the base section 412. The base section has a forward extent 414 between the support sections. The forward extent has a length greater than the length of the spaced sections.

Lastly, the system 500 is illustrated in FIG. 7 and features the support section 504 in an arcuate configuration with end points 506 spaced forwardly of the rear points (508) of the base section. The interior and exterior peripheries (510), (512) of the base section are spaced a greater distance adjacent to the rear points 508 of the base section than forwardly thereof. The support section depends downwardly from the exterior edge of the base section. The distance between the end points of the support section being less than the distance between the end points of the support section and the rear points of the base section.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A teeth separating system (200) to abate the grinding of teeth while sleeping consisting of:

a base section (202) in an arcuate configuration with a front portion positionable between the front teeth of a user and laterally spaced rear portions positionable between the rear teeth of the user, the base section having upper and lower surfaces separated by a thickness, the base section having an arcuate exterior periphery (210) with laterally spaced rear points (208), the rear points being laterally spaced by a first length, the base section having an arcuate interior periphery (212) generally concentric with the arcuate exterior periphery, the base section having a width between the arcuate interior periphery and the arcuate exterior periphery, the base section having a depth, the interior arcuate periphery (210) and the exterior arcuate periphery (212) being laterally spaced a greater distance adjacent to the laterally spaced rear points (208) and the rear teeth than forwardly of the laterally spaced rear points adjacent to the front portion and the front teeth; and a support section (204) in an arcuate configuration, the support section having inner and outer surfaces, the support section having end points (206) spaced forwardly of the rear points (208) of the base section, the inner and outer surfaces being separated by a thickness, the support section having a free first edge and a second edge separated by a height, the end points of the support section being laterally spaced by a second distance, the second distance being greater than the first length, the support section being perpendicular to and integrally formed with the base section at the arcuate exterior periphery;

the base section and the support section being fabricated in one piece of a material chosen from elasticity, the materials consisting of silicone, latex, plastic or organic materials.

* * * * *